(12) United States Patent
Moriguchi (10) Patent No.: US 7,736,620 B2
(45) Date of Patent: Jun. 15, 2010

(54) EUROPIUM-DIKETONE CHELATE COMPOUND AND FLUORESCENT MATERIAL USING THE SAME

(75) Inventor: Tetsuji Moriguchi, Kitakyushu (JP)

(73) Assignee: National University Corporation Kyushu Institute of Technology, Kitakyushu-Shi (JP)

( * ) Notice: Subject to any disclaimer, the term of this patent is extended or adjusted under 35 U.S.C. 154(b) by 53 days.

(21) Appl. No.: 11/629,386

(22) PCT Filed: Jul. 7, 2005

(86) PCT No.: PCT/JP2005/012541

§ 371 (c)(1),
(2), (4) Date: Dec. 13, 2006

(87) PCT Pub. No.: WO2006/016455

PCT Pub. Date: Feb. 16, 2006

(65) Prior Publication Data

US 2007/0244308 A1    Oct. 18, 2007

(30) Foreign Application Priority Data

Aug. 10, 2004    (JP) .............................. 2004-233137

(51) Int. Cl.
*A61B 5/00*    (2006.01)
*A61B 10/00*    (2006.01)
*A61K 49/00*    (2006.01)
(52) U.S. Cl. ......................................... 424/9.1; 424/9.6
(58) Field of Classification Search ........................ None
See application file for complete search history.

(56) References Cited

U.S. PATENT DOCUMENTS

| | | | | |
|---|---|---|---|---|
| 3,254,103 | A | * | 5/1966 | Lester et. al. .................. 534/15 |
| 5,006,503 | A | * | 4/1991 | Byers et al. .................. 503/227 |
| 7,154,007 | B2 | * | 12/2006 | Saito et al. .................... 568/42 |

FOREIGN PATENT DOCUMENTS

| | | |
|---|---|---|
| JP | 61-037885 | 2/1986 |
| JP | 64-006085 | 1/1989 |
| JP | 64-026583 | 1/1989 |
| JP | 05-255661 | 10/1993 |
| JP | 08-239609 | 9/1996 |
| JP | 10-231477 | 9/1998 |
| JP | 2004-115559 | 4/2004 |
| WO | WO 03/033447 A1 | 4/2003 |

OTHER PUBLICATIONS

Chen, X.-F. et al., Triboluminescence and crystal structures of europium (III) complexes, Materials Chemistry and Physics, 2001, 72(1), pp. 11 to 15.
Kosaburo Ohashi et al., Emission properties of ternary complexes of europium (I I I)-β- diketone- trioctylphosphine oxide, Analytical Sciences, 1990, 6(6), pp. 827 to 831.
Charles, Robert G. et al., Fluorescent europium chelates derived from fluorinated β-diketones, Journal of Inorganic and Nuclear Chemistry, 1967, 29(3), pp. 715 to 723.
Susumu Sato, et al., "Some Properties of Europium β-diketone Chelates I (Synthesis and Fluorescent Properties)", Japanese Journal of Applied Physics, vol. 7, No. 1, pp. 7-13, Jan. 1968. [Discussed in the specification].

* cited by examiner

*Primary Examiner*—Michael G Hartley
*Assistant Examiner*—Melissa Perreira
(74) *Attorney, Agent, or Firm*—Kratz, Quintos & Hanson, LLP (57) ABSTRACT

A novel europium-diketone chelate compound which steadily emits red light by ultraviolet irradiation and a fluorescent material using the same are provided. The europium-diketone chelate compound is represented by the following formula (1). The fluorescent material contains the europium-diketone chelate compound.

[Formula 1]

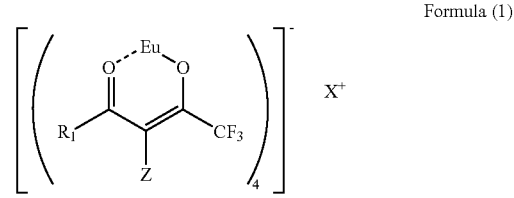

Formula (1)

wherein $X^+$ is a heterocyclic cationic polymer, a cationic oligomer or a cationic heteroaromatic compound containing a substituent, $R_1$ is an aromatic compound group or a heterocyclic compound group containing a plurality of double bonds and Z is a hydrogen atom or a substituent of an aliphatic or alicyclic compound.

1 Claim, 2 Drawing Sheets

Reaction (7)

Reaction (8)

Figure 4

EUROPIUM-DIKETONE CHELATE COMPOUND AND FLUORESCENT MATERIAL USING THE SAME

TECHNICAL FIELD

The present invention relates to a europium-diketone chelate compound and a fluorescent material using the same.

BACKGROUND ART

Today various luminescent materials are used for organic light emitting diodes, energy transducers or display elements. These luminescent materials are also used for means for preventing forgery of securities, means for inspecting contact surfaces and means for detecting trace amounts of substances.

In uses such as means for preventing forgery of securities, the luminescent materials are desired to be visually unnoticeable or colorless, but develop color and become easily visible when lighted in inspection.

Among such luminescent materials, organic materials which emit red light are conventionally known. However, most of such conventional red light emitting organic materials have a colored appearance.

In view of the problem, a method using a compound containing a europium (Eu) complex as a red light emitting organic material is disclosed.

For example, a recording liquid for inkjet using a fluorescent material comprising tetra-4,4,4-trifluoro-1-(2-thienyl)-1,3-butanedionato europium complex containing a tetra-n-butylammonium salt as a counter ion is proposed (see Patent Document 1).

The recording liquid is colorless under visible light, red at a wavelength of 600 to 650 nm under ultraviolet light having a wavelength of 254 to 365 nm, has high luminescence intensity and is excellent in light resistance.

Also, an ultraviolet-induced luminescent paste containing a europium complex using trifluoro-phenylbutanedione as a ligand is proposed (see Patent Document 2).

From its colorless appearance and emission of light by ultraviolet irradiation, the ultraviolet-induced luminescent paste is considered to have excellent visibility for determining the presence or absence of the paste.

Also, synthesis of europium-diketone chelate compounds and physical properties thereof are reported, and the report discloses that these compounds emit strong red light (see Non-Patent Document 1).

Patent Document 1: Japanese Patent Laid-Open No. 8-239609
Patent Document 2: Japanese Patent Laid-Open No. 2004-115559
Non-Patent Document 1: Susumu Sato et al, "Some Properties of Europium β-diketone Chelates I (Synthesis and Fluorescent Properties)", Japanese Journal of Applied Physics, Vol. 7, No. 1, pp. 7-13, January (1968)

However, most of the above-described conventional europium-diketone chelate compounds have high crystallinity. Such highly crystalline salts have poor processability such as coatability, film formability or dispersibility in a polymer substrate, and have problems with luminous properties such as uniformity and deterioration.

Also, while dispersibility in a polymer is required in some uses, the highly crystalline salts form particles and excellent dispersibility in a polymer cannot be achieved, often causing a problem of concentration quenching.

Moreover, the europium-diketone chelate compounds disclosed in Non-Patent Document 1 have an ionic bond, a low vapor pressure and melt or are oxidatively decomposed by heating even under reduced pressure, and therefore have a problem that the compounds cannot be formed into a film by vapor deposition.

The present invention has been made in view of the above problems and an object of the present invention is to provide a novel europium-diketone chelate compound which steadily emits red light by ultraviolet irradiation and a fluorescent material using the same.

Another object of the present invention is to provide a europium-diketone chelate compound having high dispersibility when applied to a glass substrate or mixed with plastics, and a fluorescent material using the same.

DISCLOSURE OF THE INVENTION

To achieve the above-described objects, the europium-diketone chelate compound according to the present invention is represented by the following formula (1):

[Formula 1]

wherein $X^+$ is a heterocyclic cationic polymer or a cationic oligomer, $R_1$ is an aromatic compound group or a heterocyclic compound group containing a plurality of double bonds and Z is a hydrogen atom or a substituent of an aliphatic or alicyclic compound.

Further, the europium-diketone chelate compound according to the present invention is characterized in that $X^+$ in the formula (1) is polyvinylpyridinium or a polypyrrole cation.

The europium-diketone chelate compound according to the present invention is also represented by the following formula (2):

[Formula 2]

wherein $Y^+$ is a monovalent cation, $R_2$ is a heteroaromatic group, a trisubstituted aryl group, a polyaryl group having 3 or more rings, a fused aryl group having 4 or more rings, an alkene compound group with an extended conjugated π system, an alkyne compound group with an extended conjugated π system, a cyclic or noncyclic polyether group, a complex group or a dendrimer group and Z is a hydrogen atom or a substituent of an aliphatic or alicyclic compound.

Further, the europium-diketone chelate compound according to the present invention is characterized in that $R_2$ in the formula (2) is a pyridyl group, a trialkoxyphenyl group, a terphenyl group, a pyrenyl group, a p-phenylalkynylphenyl group, a 4-stilbenyl group, a (12-crown-4)methyloxyphenyl group, a methoxytri(ethyloxy)methyloxyphenyl group or a ferrocenyl group.

The europium-diketone chelate compound according to the present invention is also represented by the following formula (3) or (4):

[Formula 3]

[Formula 4]

wherein $X^+$ is a heterocyclic cationic polymer, a cationic oligomer or a cationic heteroaromatic compound containing a substituent, $R_1$ is an aromatic compound group, a crosslinkable aromatic group or a heterocyclic compound group containing a plurality of double bonds and Z is a hydrogen atom or a substituent of an aliphatic or alicyclic compound, which is a binuclear europium-diketone chelate compound in which anions are bonded with a linker R.

Further, the europium-diketone chelate compound according the present invention is characterized in that $R_1$ in the formula (3) or (4) is an alkyl group or an alkoxy group instead of the aromatic compound group, the crosslinkable aromatic group or the heterocyclic compound group containing a plurality of double bonds.

Further, the europium-diketone chelate compound according to the present invention is characterized that the linker R is represented by the following formula (5), (6) or (7).

[Formula 5]

Formula (5)

[Formula 6]

Formula (6)

[Formula 7]

Formula (7)

The europium-diketone chelate compound according to the present invention is also represented by the following formula (8):

[Formula 8]

Formula (8)

wherein $X^{n+}$ is an n-valent cationic polymer, Ar is a substituted aromatic group, a fused aromatic group or a heterocyclic aromatic group and Z is a hydrogen atom or a substituent of an aliphatic or alicyclic compound.

Further, the europium-diketone chelate compound according to the present invention is characterized in that $X^{n+}$ is polyvinylpyridinium or a polypyrrole cation.

The fluorescent material according to the present invention is characterized by comprising the above-described europium-diketone chelate compound.

The fluorescent material according to the present invention contains a novel europium-diketone chelate compound which steadily emits red light by ultraviolet irradiation.

Also, the fluorescent material containing the europium-diketone chelate compound according to the present invention has high dispersibility when applied to a glass substrate or mixed with plastics.

BEST MODE FOR CARRYING OUT THE INVENTION

Embodiments of the present invention are described below with reference to Examples.

EXAMPLE 1

Example of a europium-diketone chelate compound represented by the following formula (8) and a fluorescent material containing the europium-diketone chelate compound according to the present invention is described.

[Formula 8]

Formula (8)

The europium-diketone chelate compound of this Example is a compound in which $X^{n+}$ is a n-valent polymer cation, Ar is a substituted aromatic group, a fused aromatic group or a heterocyclic aromatic group and Z is a hydrogen atom or a substituent of an aliphatic or alicyclic compound in the formula (8).

The process for producing the compound and the fluorescent layer in which the compound is used as a fluorescent material and their properties are described in detail referring to a compound in which $X^{n+}$ in the formula (8) is polyvinylpyridinium, namely, a polyvinylpyridinium.tetrakis (aryltrifluoromethyl propanedionato) europate compound (hereinafter PVPEu compound) represented by the following formula (9).

[Formula 9]

Formula (9)

The process for producing the PVPEu compound is described with reference to the reaction scheme in FIG. 1.

Figure 1:
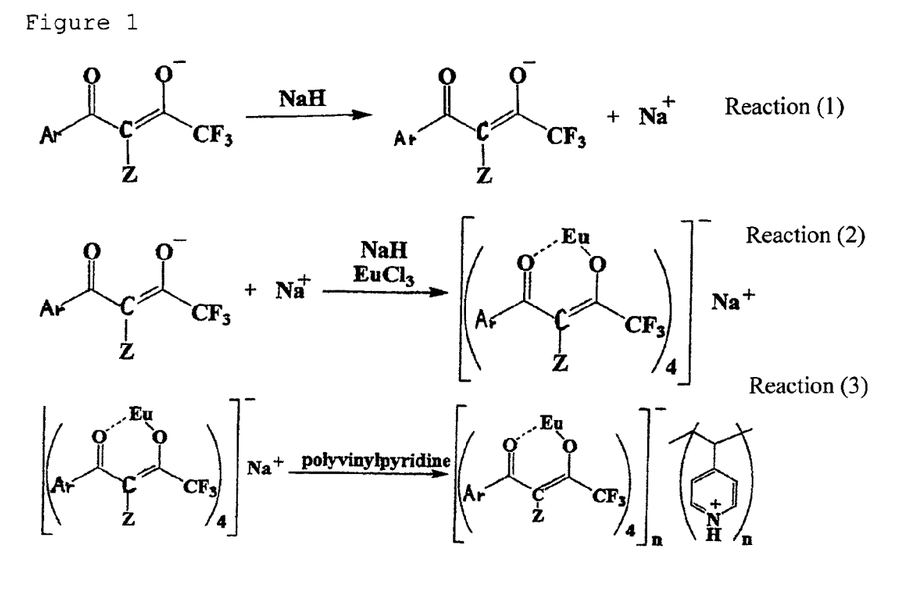
FIG. 1 illustrates a reaction scheme for the europium-diketone chelate compound of Example 1.

20 ml of a solution of 2.0 mM diketone ligand (Ar—CO—CZ—CO—CF$_3$, Ar is a fluorenyl group, Z is a hydrogen atom) in dichloromethane was added dropwise to 50 ml of a solution of 8.0 mM degreased sodium hydride in methanol-dichloromethane, and the mixture was stirred at room temperature for 10 minutes (reaction (1) in FIG. 1).

Subsequently, 10 ml of a solution of 0.50 mM europium chloride in methanol was added dropwise to the reaction solution prepared in the reaction (1), and the mixture was stirred at room temperature for additional 10 minutes (reaction (2) in FIG. 1).

Then, 4.5 ml of a solution of 0.50 mM polyvinylpyridine in dichloromethane was added dropwise to the reaction mixture prepared in the reaction (2), and the mixture was stirred for additional 10 hours so that the resulting polymer solid was dispersed (reaction (3) in FIG. 1).

The solvent was completely removed by subjecting the solution prepared in the reaction (3) to reduced pressure to give a solid. Subsequently, dichloromethane was added to the solid and the solid was suspended in dichloromethane.

The solid in the suspension was filtered to give polymer precipitate. The polymer precipitate was washed with water to remove the byproduct, sodium chloride, and then dissolved in methanol, and the insoluble matters were removed by filtration. The methanol solution from which the insoluble matters were removed was subjected to reduced pressure to remove methanol, whereby a PVPEu compound in the form of a polymer solid was obtained. The yield of the PVPEu compound was 80%.

The resulting PVPEu compound was colorless and emitted red light when irradiated with ultraviolet light (black light).

The PVPEu compound was insoluble in solvents such as benzene, toluene, dichloromethane, acetone, chloroform and hexane, but soluble in alcohol solvents such as ethanol, methanol and isopropanol and polar protic organic solvents such as dimethyl sulfoxide, dimethylformamide and N-methylpyrrolidone. The PVPEu compound was insoluble in water.

The PVPEu compound was amorphous.

Next, a process for producing a fluorescent layer in which a fluorescent material containing the PVPEu compound is used and properties of the layer are described below.

0.10 g of the PVPEu compound was dissolved in 10 ml of ethanol and the solution was applied to a 2.0 mm×2.0 mm glass plate and dried. The PVPEu compound formed a transparent fluorescent layer without crystallizing in the coating film. In this case, methanol may be used instead of ethanol.

The resulting fluorescent layer emitted red light when irradiated with ultraviolet light (black light).

The PVPEu compound may be mixed with a toluene.ethyl acetate adhesive or an alcohol-based coating, and a fluorescent layer may be formed by applying and drying the mixed coating.

The above PVPEu compound was each dispersed in a melt of polypropylene and polyethylene. The resin in which the PVPEu compound was dispersed was cooled to give a transparent resin product having a uniform composition.

The transparent resin product emitted red light when irradiated with ultraviolet light (black light).

The results of evaluation of amorphous properties, film formability, luminescence intensity, film durability and dispersibility in polymer substrates of the PVPEu compound and the fluorescent layer containing the PVPEu compound are shown in the column of Example 1(1) in Table 1.

Herein, the amorphous properties were evaluated using a melting-point measuring apparatus and a differential scanning calorimeter (DSC). "G (good)" means those without crystallization at room temperature, "M (moderate)" means those which crystallized in a specific solvent or did not crystallize but showed phase transition, and "P (poor)" means those which easily crystallized at room temperature.

The film formability was evaluated visually or by a microscope as to whether the transparency was maintained after direct application to the surface of a glass substrate or spin coating. "G" means those which are transparent and not powdered, "M" means those which are semi-transparent and partly powdered, and "P" means those which are opaque and powdered.

The luminescence intensity was evaluated based on comparison with the luminescence quantum yield of a control compound using a fluorescence measuring apparatus. "G" means those having a higher intensity than that of the control compound, "M" means those having about the same intensity as that of the control compound and "P" means those having a slightly lower intensity than that of the control compound.

The film durability was evaluated by visual observation of generation of crack or peeling after touching the film formed on a glass substrate or a resin board with the finger or slightly bending the substrate. "G" means those without any change, "M" means those with either peeling or crack and "P" means those with significant peeling and crack.

TABLE 1

| | X+ | R₁ | Amorphous properties | Film formability | Luminescence intensity | Film durability | Dispersibility in polymer substrate |
|---|---|---|---|---|---|---|---|
| | | | Example 1 | | | | |
| 1 |  |  | G | G | G | G | G |
| 2 |  | R = C₁₂H₂₅ | G | G | G | G | G |
| 3 |  | R = C₁₂H₂₅ | G | G | G | G | G |
| | | | Example 2 | | | | |
| 4 |  | R = C₁₂H₂₅ | G | M | G | M | G |
| 5 |   R₁ = alkyl, aryl etc. |  | M | M | G | M | G |
| 6 |   R₁ = alkyl, aryl etc. |  | M | M | G | M | G |
| 7 |   R₁ = alkyl, aryl etc. | R = C₁₂H₂₅ | G | M | G | M | G |
| | | | Comparative Example 1 | | | | |
| 1 | butylammonium | (thiophene) | P | P | G | P | P |
| 2 | piperidinium | H₃C—⟨benzene⟩— | P | P | G | P | P |

Although not shown in Table 1, the effect similar to that described above could be obtained even if a cation polymer such as a polypyrrole cation, polyvinylammonium (the following formula (10)), polyallylammonium (the following formula (11)) or a cation polymer (the following formula (12)) in which a proton is bonded to a nitrogen atom of polyethyleneimine is used instead of the above-described polyvinylpyridinium.

[Formula 10]

[Formula 11]

[Formula 12]

Also, the same test as described above was each performed for a combination in which $X^+$ was polyvinylpyridinium and $R_1$ was dodecyloxyphenyl and a combination in which $X^+$ was a polypyrrole cation and $R_1$ was dodecyloxyphenyl in the formula (1). Z was a hydrogen atom or a methyl group derived from an aliphatic compound in both cases. Properties of the PVPEu compound and the fluorescent layer containing the PVPEu compound obtained in the test are shown in the columns of Example 1(2) and Example 1(3) in Table 1.

EXAMPLE 2

Example of a europium-diketone chelate compound represented by the following formula (1) and a fluorescent material containing the europium-diketone chelate compound according to the present invention is described.

[Formula 1]

Formula (1)

The europium-diketone chelate compound of this Example is a compound in which $X^+$ is a heterocyclic cationic polymer, a cationic oligomer or a cationic heteroaromatic compound containing a substituent and $R_1$ is an aromatic compound group or a heterocyclic compound group containing a plurality of double bonds. The compounds in the compound group of $X^+$ and the compounds in the compound group of $R_1$ and Z and the substituents may be employed in any combination.

A compound and a fluorescent layer in which the compound was used as a fluorescent material were prepared and evaluated using, as examples, combinations in which $X^+$ is bipyridinium and $R_1$ is dodecyl, $X^+$ is alkylpyridinium, $R_1$ is a terphenyl group and Z is a hydrogen atom, $X^+$ is alkylpyridinium and $R_1$ is a fluorenyl group, and $X^+$ is alkylpyridinium, $R_1$ is dodecyl and Z is a hydrogen atom in the formula (1).

The compound and the fluorescent layer in which the compound was used as a fluorescent material were prepared by the same process as in Example 1.

As shown in the columns of Example 2(4), Example 2(5), Example 2(6) and Example 2(7) in Table 1, the resulting fluorescent layers showed almost the same results as in Example 1 although the film formability and the film durability were slightly lower.

COMPARATIVE EXAMPLE 1

The same test as in Example 2 was performed with combinations in which $X^+$ is butylammonium, $R_1$ is a thiophene group and Z is a hydrogen atom and $X^+$ is piperidinium, $R_1$ is a p-methylphenyl group and Z is a hydrogen atom in the formula (1).

The resulting compound had good luminescence intensity but was crystalline. The fluorescent layer had poor film formability, poor film durability and poor dispersibility in a polymer substrate. The results are shown in the columns of Comparative Examples 1(1) and (2) in Table 1.

EXAMPLE 3

Example of a europium-diketone chelate compound represented by the following formula (2) and a fluorescent material containing the europium-diketone chelate compound according to the present invention is described.

[Formula 2]

Formula (2)

The europium-diketone chelate compound of this Example is a compound in which $Y^+$ is a monovalent cation, Z is a hydrogen atom, $R_2$ is a heteroaromatic group, a trisubstituted aryl group, a polyaryl group having 3 or more rings, a fused aryl group having 4 or more rings, a fluorenyl group, an alkene compound group with an extended conjugated π system, an alkyne compound group with an extended conjugated π system, a cyclic or noncyclic polyether group, a complex group or a dendrimer group.

A compound in which $Y^+$ is a cation, Z is a hydrogen atom and $R_2$ is a substituted aromatic group, a fused aromatic group or a heterocyclic aromatic group shown in the following substituent group, namely, $Y^+$.tetrakis($R_2$-trifluoromethyl-propanedionato) europate (hereinafter $Y^+TR_2Eu$ compound) and a fluorescent layer in which the compound was used as a fluorescent material were prepared and evaluated as an example.

[Formula 24]

The process for producing the $Y^+ \cdot TR_2Eu$ compound is described with reference to the reaction scheme in FIG. 2.

Figure 2:
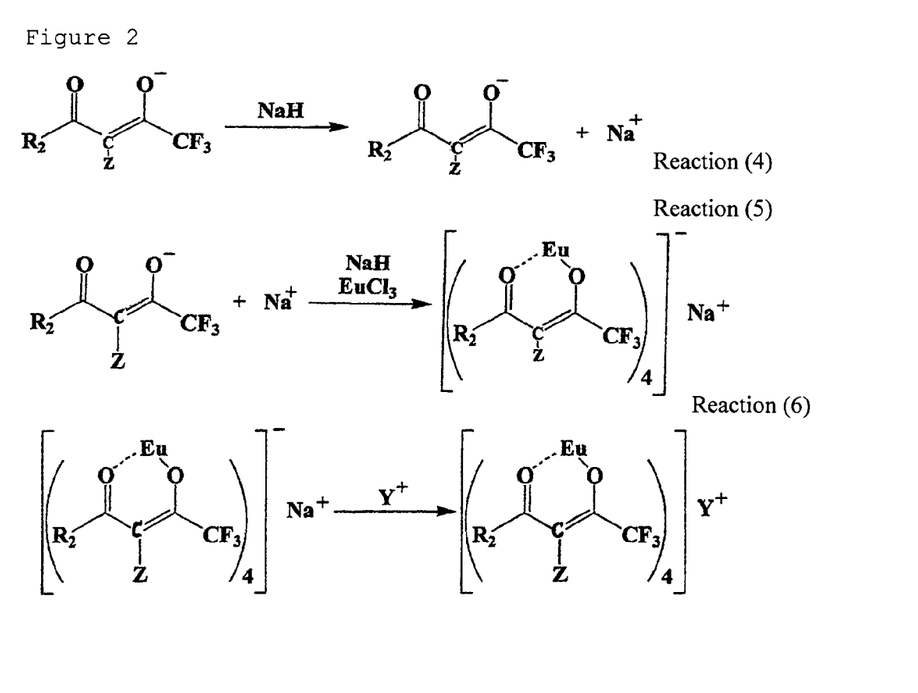
FIG. 2 illustrates a reaction scheme for the europium-diketone chelate compound of Example 2.

20 ml of a solution of 2.0 mM diketone ligand ($R_2$—CO—CZ—CO—CF$_3$, in which $R_2$ is a pyridinyl group and Z is a hydrogen atom) in dichloromethane was added dropwise to 50 ml of a solution of 8.0 mM degreased sodium hydride in methanol-dichloromethane, and the mixture was stirred at room temperature for 10 minutes (reaction (4) in FIG. 2).

Subsequently, 10 ml of a solution of 0.50 mM europium chloride in methanol was added dropwise to the reaction solution prepared in the reaction (4), and the mixture was stirred at room temperature for additional 10 minutes (reaction (5) in FIG. 2).

Then, 4.5 ml of a solution of 0.50 mM base (piperidine in this case) which is a counter cation in dichloromethane was added dropwise to the reaction mixture prepared in the reaction (5), and the mixture was stirred for additional 10 hours (reaction (6) in FIG. 2).

The precipitate produced in the reaction (6) was filtered under reduced pressure and washed with water to remove the byproduct, hydrochloride, whereby the intended $Y^+ \cdot TR_2Eu$ compound was obtained (piperidinium(thiophenyl-trifluoromethylpropanedionato) europate in this case). The average yield of the compound was 80%.

The resulting $Y^+ \cdot TR_2Eu$ compound was colorless and emitted red light when irradiated with ultraviolet light (black light).

The $Y^+ \cdot TR_2Eu$ compound was soluble in solvents such as benzene, toluene, dichloromethane, acetone, chloroform and hexane, but hardly soluble in alcohol solvents such as ethanol, methanol and isopropanol and easily soluble in polar protic organic solvents such as dimethyl sulfoxide, dimethylformamide and N-methylpyrrolidone. The $Y^+ \cdot TR_2Eu$ compound was insoluble in water.

Properties of the $Y^+ \cdot TR_2Eu$ compound are shown in the column of Example 3(1) in Table 2.

TABLE 2

| | Y+ | R₂ | Light emission ON/OFF ability | Luminescence intensity | Dispersibility in polymer substrate | Film properties |
|---|---|---|---|---|---|---|
| | | Example 3 | | | | |
| 1 | piperidinium | (3-methylpyridine) | G | G | M | P |
| 2 | piperidinium | (4-methyl-p-terphenyl) | M | G | G | G |
| 3 | pyridinium | (trialkoxytoluene, R = C₄H₉) | G | G | G | G |
| 4 | piperidinium | (1-methylpyrene) | G | G | M | P |
| 5 | pyridinium | (2-methylfluorene) | G | G | M | P |
| 6 | piperidinium | (4-methyldiphenylacetylene) | M | G | M | M |
| 7 | piperidinium | (4-methylstilbene) | M | G | M | M |
| 8 | piperidinium | (crown ether derivative, n = 1) | G | G | G | G |
| 9 | piperidinium | (glycol ether derivative, n = 1) | G | G | G | G |

TABLE 2-continued

| | $Y^+$ | $R_2$ | Light emission ON/OFF ability | Luminescence intensity | Dispersibility in polymer substrate | Film properties |
|---|---|---|---|---|---|---|
| 10 | piperidinium | (ferrocenyl) | G | M | M | M |
| | | Comparative Example 2 | | | | |
| 3 | butylammonium | (2-thienyl) | P | G | P | P |
| 4 | piperidinium | (4-methylphenyl) | P | G | P | P |

Herein, introduction of a methyl group into Z suppresses fading of light emission of the compound in sunlight by a few tens of percent.

Generally, most of light emitting elements are chemically changed and faded due to exposure to sunlight in the presence of oxygen. This is attributable to the fact that an organic compound excited by ultraviolet light is easily oxidized in the presence of oxygen. The weatherability becomes a problem in some uses, and therefore the problem has been solved by introducing substituent Z into the skeleton of the compound. The solubility, the luminescence intensity and the dispersibility were not very different from those of a compound in which Z is a hydrogen atom.

Also, $Y^+ \cdot TR_2Eu$ compounds were synthesized by the same synthetic method as described above with combinations in which $Y^+$ was piperidinium or pyridinium and $R_2$ each was a substituent of the above substituent group in the formula (2). The resulting $Y^+ \cdot TR_2Eu$ compounds were amorphous except for those in which the substituent was trialkoxyphenyl (1), methoxypolyethoxy phenyl (7), crown ether (10) or dendrimer (11).

Of the $Y^+ \cdot TR_2Eu$ compounds obtained, 0.10 g of the amorphous compounds was each dissolved in 10 ml of dimethyl sulfoxide and the resultant was applied to a 2.0 mm×2.0 mm glass plate and dried. The $Y^+ \cdot TR_2Eu$ compounds formed a transparent fluorescent layer without crystallizing in the coating film.

The resulting fluorescent layer emitted red light when irradiated with ultraviolet light (black light).

The $Y^+ \cdot TR_2Eu$ compound may be mixed with a toluene-.ethyl acetate adhesive or acrylic coating, and a fluorescent layer may also be formed by applying and drying the mixed coating.

Further, the $Y^+ \cdot TR_2Eu$ compound was dispersed in a melt of a resin such as polypropylene and polyethylene. The resin in which the $Y^+ \cdot TR_2Eu$ compound was dispersed was cooled to give a transparent resin product having a uniform composition. The transparent resin product emitted red light when irradiated with ultraviolet light (black light).

The $Y^+ \cdot TR_2Eu$ compounds having fluorenyl (2), terphenyl (5), phenylethynylphenyl (6), or stilbenyl (8) as a substituent are shown in the following formulas (13) to (16). Although these compounds are crystalline as described above, the compounds have, of the light emitting properties, control of excitation wavelength and ability to detect molecules or ions utilizing the space surrounded by the extended π electron system of four ligands.

[Formula 13]

[Formula 14]

[Formula 15]

-continued

Formula (16)

[Formula 16]

In the $Y^+.TR_2Eu$ compounds, control of fluorescence excitation wavelength, which was limited in the conventional art, became possible because the π conjugated system in the ligand was changed to an extended type. More specifically, the excitation wavelength of the $Y^+.TR_2Eu$ compounds was each 356, 349, 375 and 360/285 nm. Optical properties of the $Y^+.TR_2Eu$ compounds are shown in Table 3.

TABLE 3

| Complex | Excitation wavelength/ nm | Emission wavelength/ nm | Luminescence intensity/ intensity/a.u. | Luminescence quantum yield/φem |
|---|---|---|---|---|
| Formula (13) | 356 | 615 | 3009 | 51% |
| Formula (14) | 349 | 615 | 3040 | 51% |
| Formula (15) | 375 | 615 | 3122 | 52% |
| Formula (16) | trans/cis 360/285 | 615 | trans/cis 3200/2995 | trans/cis 54%/50% |

In the $Y^+.TR_2Eu$ compounds containing pyridine (4) or crown ether (10) shown in the above substituent group as a substituent, as the pyridine substituent is protonated in an acidic condition, the energy level of the ligands is changed, and therefore the compounds have pH-dependant light emission switching ON-OFF ability in an organic solvent, which was conventionally difficult to achieve. The light emission is OFF in an acidic condition and ON in an alkaline condition.

The $Y^+.TR_2Eu$ compounds also have ability to form a complex with metal ions of platinum or gold, and the light emission is switched off or on when the ions are captured. Ions can also be captured and detected by a film carrying the complex or the complex itself even in an aqueous system.

In the $Y^+.TR_2Eu$ compounds containing a ferrocenyl (9) substituent shown in the above substituent group, as the valence of the ferrocenyl substituent is changed in a redox condition, the energy level of the ligands is changed, and therefore the compounds have redox potential-dependant light emission switching ON-OFF ability in an organic solvent, which was conventionally difficult to achieve. The light emission is OFF in an oxidizing condition and ON in a reducing condition.

Also, the $Y^+.TR_2Eu$ compound containing a dendrimer (n generation: n is any number) (11) substituent shown in the above substituent group has a high and stable luminescence intensity and excellent solvent dispersibility and solubility, and the light emission is not affected from other chemical species. Although the linking portion in the dendrimer is an ether bond, another linker may be present.

The condition of combining $Y^+$ and $R_2$ for synthesizing the $Y^+.TR_2Eu$ compounds and properties of the compounds are shown in the columns of Example 3(2), Example 3(3), Example 3(4), Example 3(5), Example 3(6), Example 3(7), Example 3(8), Example 3(9) and Example 3(10) in Table 2.

COMPARATIVE EXAMPLE 2

The same test as in Example 3 was performed with combinations in which $Y^+$ is butylammonium, $R_2$ is a thiophene group and Z is a hydrogen atom and $Y^+$ is piperidinium, $R_2$ is a p-methylphenyl group and Z is a hydrogen atom in the formula (2).

Properties of the resulting. $Y^+.TR_2Eu$ compounds are shown in the columns of Comparative Example 2(3) and Comparative Example 2(4) in Table 2. The $Y^+.TR_2Eu$ compounds have good luminescence intensity but do not have light emission ON/OFF ability, and have poor dispersibility in a polymer substrate and poor film properties.

EXAMPLE 4

Example of a europium-diketone chelate compound represented by the following formula (3) and a fluorescent material containing the europium-diketone chelate compound according to the present invention is described.

[Formula 29]

Formula (3)

The europium-diketone chelate compound of this Example is a binuclear europium-diketone chelate compound in which anions are bonded with a linker R, $X^+$ is a heterocyclic cationic polymer, a cationic oligomer or a cationic heteroaromatic compound containing a substituent and $R_1$ is an aromatic compound group, a crosslinkable aromatic group, a heterocyclic compound group containing a plurality of double bonds, an alkyl group or an alkoxy group, and Z is a hydrogen atom. The compounds in the compound group of $X^+$ and the compounds in the compound group of Z and $R_1$ and the substituents may be employed in any combination.

A compound in which $X^+$ is piperidinium, $R_1$ is a p-phenylene group, Z is a hydrogen atom and linker R is a substituent shown in the following substituent group and a fluorescent layer in which the compound was used as a fluorescent material were prepared and evaluated as an example.

[Formula 30]

-continued

The process for producing the above compound (complex) is described with reference to the reaction scheme in FIG. 3.

Figure 3:
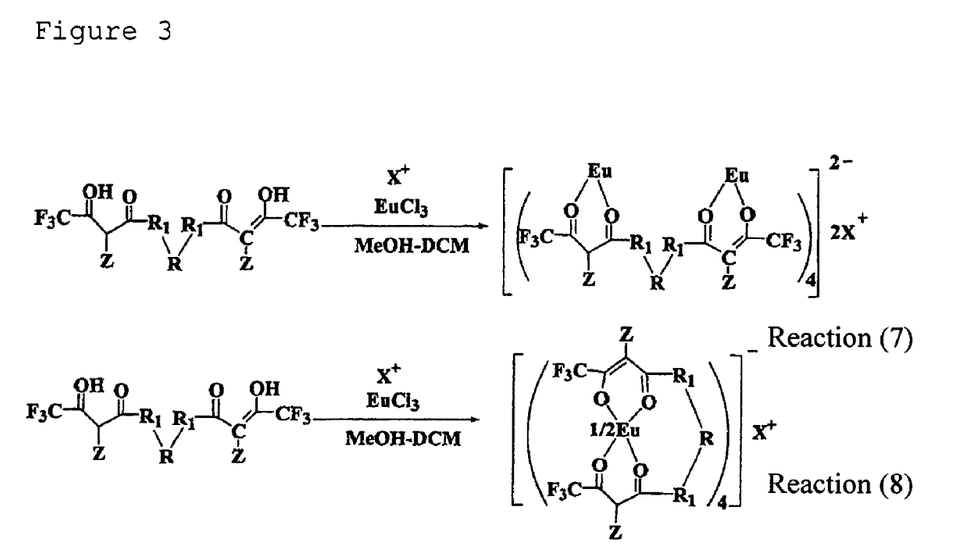
FIG. 3 illustrates a reaction scheme for the europium-diketone chelate compound of Example 3 according to the present invention.
Figure 4:
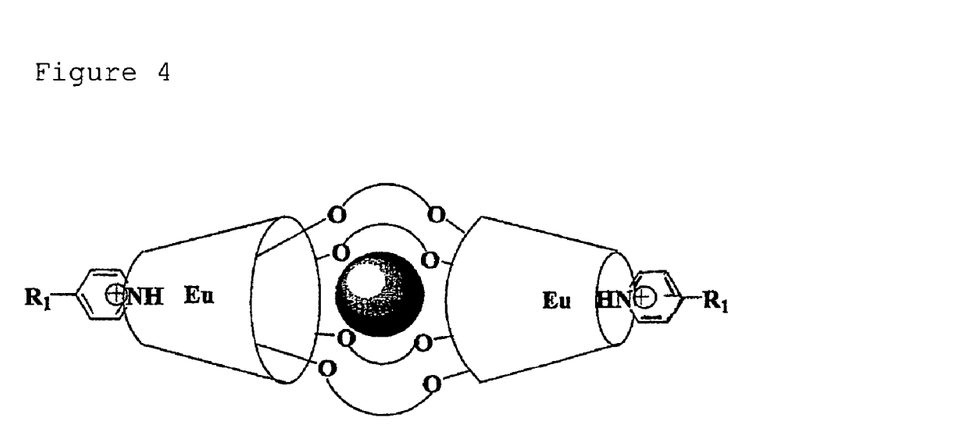
FIG. 4 illustrates an example of europium-diketone chelate compounds of Example 4.

20 ml of a dichloromethane solution of 1.0 mM bisdiketone ligand in which $R_1$ is a p-phenylene group, Z is a hydrogen atom and linker R is represented by the following formula (17) in the formula (3) was added dropwise to 50 ml of a methanol-dichloromethane solution, and the mixture was stirred at room temperature for 10 minutes (reaction (7) in FIG. 3).

[Formula 17]

Formula (17)

Subsequently, 10 ml of a solution of 0.50 mM europium chloride in methanol was added dropwise to the reaction solution, and the mixture was stirred at room temperature for additional 10 minutes. Then, a solution of 0.50 mM piperidine, a base which is a counter cation, in dichloromethane was added dropwise to the reaction mixture, and the mixture was stirred at room temperature for additional 10 hours (reaction (8) in FIG. 3).

The resulting precipitate was filtered under reduced pressure and washed with water to remove the byproduct, hydrochloride, whereby a complex was obtained at an average yield of 80%.

The resulting complex was colorless and emitted red light when irradiated with ultraviolet light (black light).

The complex was soluble in solvents such as benzene, toluene, dichloromethane, acetone, chloroform and hexane, but hardly soluble in alcohol solvents such as ethanol, methanol and isopropanol and easily soluble in polar protic organic solvents such as dimethyl sulfoxide, dimethylformamide and N-methylpyrrolidone. The complex was insoluble in water.

0.10 g of the complex was dissolved in 10 ml of dimethyl sulfoxide and the solution was applied to a 2.0 mm×2.0 mm glass plate and dried. The complex formed a transparent fluorescent layer without crystallizing in the coating film. The fluorescent layer emitted red light when irradiated with ultraviolet light (black light).

Similar results could be obtained using ethanol instead of dimethyl sulfoxide as the solvent.

The complex may be mixed with a toluene.ethyl acetate adhesive or an acrylic coating, and a fluorescent layer may be formed by applying and drying the mixed coating.

Properties of the complex are shown in the columns of Example 4(1) to Example 4(3) and Example 4(5) to Example 4(7) in Table 4.

Herein, the host-guest function was evaluated by liquid-liquid extraction with metal picrate by ultraviolet and visible absorption spectrum measurement. "G" means a state in which the complex was completely extracted in the existing organic solvent, "M" means a state in which part of the organic solvent was colored and "P" means a state in which no extraction occurred and the solvent was not colored.

Also, the complex forming ability was evaluated by ultraviolet and visible absorption spectrum measurement based on a reaction as to whether the complex was capable of forming a binuclear complex with a salt of heavy metal such as ruthenium or platinum. "G" means that a binuclear complex was formed and a new absorption appeared, "M" means that changes were observed and "P" means that no change was observed at all.

The luminescence intensity was evaluated based on comparison with the luminescence quantum yield of a control compound using a fluorescence measuring apparatus. "G" means those having a higher intensity than that of the control compound, "M" means those having about the same intensity as that of the control compound and "P" means those having a slightly lower intensity than that of the control compound.

The dispersibility in a polymer substrate was evaluated visually or by a microscope as to whether the transparency was maintained after dissolving and dispersing in a molten polypropylene or an araldite adhesive. "G" means those which are transparent and not powdered, "M" means those which are semi-transparent and partly powdered, and "P" means those which are opaque and powdered.

TABLE 4

| | X+ | R₁ | Linker R | Host-guest function | Complex forming ability | Luminescence intensity | Dispersibility in Film polymer substrate | properties |
|---|---|---|---|---|---|---|---|---|
| | | | Example 4 | | | | | |
| 1 | piperidinium | (p-tolyl) | -CH₂-O-CH₂-(p-phenylene)-CH₂-O-CH₂- | G | P | G | M | M |
| 2 | piperidinium | (p-tolyl) | -CH₂-O-CH₂-(2,6-naphthylene)-CH₂-O-CH₂- | G | P | G | G | M |
| 3 | piperidinium | (p-tolyl) | -CH₂-O-CH₂-(9,10-anthrylene)-CH₂-O-CH₂- | G | P | G | M | M |
| 4 | piperidinium | (p-tolyl) | -CH₂-O-CH₂CH₂-O-CH₂CH₂-O-CH₂- | G | G | G | G | G |
| 5 | piperidinium | (p-tolyl) | -CH₂-O-CH₂-(3,5-pyridylene)-CH₂-O-CH₂- | P | G | G | M | M |
| 6 | piperidinium | (p-tolyl) | -CH₂-O-CH₂-(2,6-pyridylene)-CH₂-O-CH₂- | P | G | G | M | M |
| 7 | piperidinium | (p-tolyl) | -CH₂-O-CH₂-(CH₂)₄-CH₂-O-CH₂- | G | P | G | G | G |

Also, a binuclear compound as shown in FIG. 3 can be formed by four crosslinking groups (linkers) as the compound (complex) represented by the formula (3).

The binuclear compound has ability to capture cations therein as a guest. The binuclear compound can also capture metal cations such as K, Na and Ca, heavy transition metal cations such as Cu and Ru, organic aromatic cations and organic neutral guests as the guest. Since the Eu luminescence intensity of the complex changes due to such guests that have been captured, the complex may also be used for qualitative or quantitative analysis of the guest. In particular, when the crosslinking moiety of the complex is an aromatic compound, the complex is generally compatible with an organic N-alkyl salt guest such as methylpyridinium. The state of electrons in the crosslinking aromatic compound changes by complexation with the guest, and this remotely affects the excitation energy at the ligand moiety through space, and therefore the luminescence intensity significantly changed after complexation.

Properties of the complex are shown in the column of Example 4(4) in Table 4.

The invention claimed is:

1. A fluorescent material comprising a europium-diketone chelate compound represented by the following formula (3) or (4):

[Formula 3]

-continued

[Formula 4]

wherein X⁺ is a heterocyclic cationic polymer, a cationic oligomer or a cationic heteroaromatic compound, $R_1$ is an alkyl group or an alkoxy group, Z is a hydrogen atom or a substituent of an aliphatic or alicyclic compound and R is selected from the group consisting of for the europium-diketone chelate compound of formula (3) and R is selected from the group consisting of for the europium-diketone chelate compound of formula (4).

* * * * *